United States Patent
Ciallella et al.

(10) Patent No.: US 11,484,541 B2
(45) Date of Patent: Nov. 1, 2022

(54) NUTRACEUTICAL COMPOSITION FOR THE ACTIVATION OF SIRTUINS WITH ANTI-AGING/REVERSE-AGING EFFECT

(71) Applicant: SIRTLIFE CORP., New York, NY (US)

(72) Inventors: Giovanni Ciallella, Rome (IT); Lyudmyla Zaporozhets, Rome (IT)

(73) Assignee: SIRTLIFE CORP., New York, NY (US)

( * ) Notice: Subject to any disclaimer, the term of this patent is extended or adjusted under 35 U.S.C. 154(b) by 16 days.

(21) Appl. No.: 16/961,963

(22) PCT Filed: Jan. 8, 2019

(86) PCT No.: PCT/IB2019/050119
§ 371 (c)(1),
(2) Date: Jul. 14, 2020

(87) PCT Pub. No.: WO2019/138317
PCT Pub. Date: Jul. 18, 2019

(65) Prior Publication Data
US 2020/0352969 A1    Nov. 12, 2020

(30) Foreign Application Priority Data

Jan. 15, 2018 (IT) ......................... 102018000000890

(51) Int. Cl.
| | | |
|---|---|---|
| A61K 31/7034 | (2006.01) | |
| A23L 33/105 | (2016.01) | |
| A23L 33/16 | (2016.01) | |
| A23L 33/15 | (2016.01) | |
| A61K 9/20 | (2006.01) | |
| A61K 31/05 | (2006.01) | |
| A61K 31/09 | (2006.01) | |
| A61K 31/352 | (2006.01) | |
| A61K 31/455 | (2006.01) | |
| A61K 33/04 | (2006.01) | |
| A61K 33/30 | (2006.01) | |
| A61K 36/45 | (2006.01) | |
| A61K 36/575 | (2006.01) | |
| A61K 36/704 | (2006.01) | |

(52) U.S. Cl.
CPC ........ *A61K 31/7034* (2013.01); *A23L 33/105* (2016.08); *A23L 33/15* (2016.08); *A23L 33/16* (2016.08); *A61K 9/2009* (2013.01); *A61K 9/2013* (2013.01); *A61K 9/2054* (2013.01); *A61K 9/2072* (2013.01); *A61K 31/05* (2013.01); *A61K 31/09* (2013.01); *A61K 31/352* (2013.01); *A61K 31/455* (2013.01); *A61K 33/04* (2013.01); *A61K 33/30* (2013.01); *A61K 36/45* (2013.01); *A61K 36/575* (2013.01); *A61K 36/704* (2013.01)

(58) Field of Classification Search
CPC .............. A61K 31/7034; A61K 9/2009; A61K 9/2013; A61K 9/2054; A61K 9/2072; A61K 31/05; A61K 31/09; A61K 31/352; A61K 31/455; A61K 33/04; A61K 33/30; A61K 36/45; A61K 36/575; A61K 36/704; A23L 33/105; A23L 33/16; A23L 33/15
USPC .......................................................... 514/23
See application file for complete search history.

(56) References Cited

U.S. PATENT DOCUMENTS

| | | |
|---|---|---|
| 2004/0047896 A1 | 3/2004 | Malnoe et al. |
| 2005/0100617 A1 | 5/2005 | Malnoe et al. |
| 2012/0177730 A1* | 7/2012 | Baron .................. A61K 9/0053 424/452 |
| 2016/0045561 A1 | 2/2016 | Larsen-Vefring et al. |

FOREIGN PATENT DOCUMENTS

| | | |
|---|---|---|
| DE | 10 2013 205049 A1 | 6/2013 |
| WO | 02/071874 A2 | 9/2002 |

OTHER PUBLICATIONS

Baños et al. Medicinal Agents in the Metabolic Syndrome. Cardiovascular & Hematological Agents in Medicinal Chemistry, 2008, 6, 237-252. (Year: 2008).*
International Preliminary Report on Patentability dated Jul. 30, 2020, from corresponding PCT application No. PCT/IB2019/050119.
Shen et al., "Anti-ageing active ingredients from herbs and nutraceuticals used in traditional Chinese medicine: pharmacological mechanisms and implications for drug discovery", British Journal of Pharmacology, 2017, pp. 1395-1425, vol. 174, No. 11.
International Search Report and Written Opinion, dated Mar. 6, 2019, from corresponding PCT application No. PCT/IB2019/050119.

* cited by examiner

*Primary Examiner* — Yih-Horng Shiao
(74) *Attorney, Agent, or Firm* — Nixon & Vanderhye

(57) ABSTRACT

Nutraceutical composition for the activation of sirtuins in humans, the composition including from 10% by weight to 15% by weight of honokiol; from 12% by weight to 40% by weight of pterostilbene; from 22% by weight to 32% by weight of polydatin; from 25% by weight to 40% by weight of ellagic acid and from 1.5% by weight to 3% by weight of a mixture of zinc, seleniun, chromium and nicotinamide, the composition promoting the inhibition of cell degradation and aging phenomena.

20 Claims, No Drawings

NUTRACEUTICAL COMPOSITION FOR THE ACTIVATION OF SIRTUINS WITH ANTI-AGING/REVERSE-AGING EFFECT

FIELD OF THE INVENTION

The present invention relates to the nutraceutical field and in particular to a peculiar composition comprising the ingredients which, besides being beneficial for the human organism when taken singly, involve, when co-existent in particular concentrations as in the subject composition, a consistent activation of sirtuins, giving rise to all the anti-degenerative, anti-aging, and reverse-aging effects triggered by the activation.

PRIOR ART

It is undoubted that over the centuries the average life of individuals has consistently increased. This remarkable difference cannot be attributed to genetic variations of the human species, but it can certainly be traced back to changes of an environmental nature, such as the improvement of living conditions and the progress of medicine.

Aging can be defined as the complex of all the physiological, genetic and molecular changes that occur with the passing of time. Age-dependent changes can be attributed to the natural process of growth, to genetic defects related to the individual, to the relationship between genotype and environment. Our body is continuously subjected to oxidative stress, due to oxidizing substances (free radicals) that are generated as a result of environmental factors (UV rays) or substances introduced with the diet or that are produced inside the cells during cell respiration. Free radicals are formed in every moment of our life and from the moment of birth, in relation to the normal life processes of cellular respiration and other factors such as excessive physical exercise, active and passive cigarette smoking, electromagnetic pollution, atmospheric pollution, an infinite variety of chemicals in the air and in food.

Oxidative stress induces strong damages to proteins, lipids and DNA, increasing the risk of tumors, cardiovascular diseases and degenerative diseases in general. Once damaged, the cell defends itself from damage by activating repair mechanisms or, if the damage is excessive, activating a programmed death program, apoptosis, whose purpose is to permanently eliminate the diseased cell. It has long been known that, during aging, there is a progressive increase in cellular damage due to oxidative stress. From a molecular point of view, the increase in oxidative stress associated with age can be traced to three different factors: an increase in the rate at which reactive oxygen metabolites are produced, a decline in antioxidant defense systems and a decreased efficiency in degrading and repairing damaged molecules. ROS (Reactive Oxygen Species) are very reactive chemical species, present in the environment and also generated in the body as by-products of metabolism, especially during mitochondrial respiration. ROS are involved in the pathogenesis of a range of diseases, from inflammation to immunosuppression, from diabetes to Alzheimer's disease, from cirrhosis to atherosclerosis and various types of cancer (Lyras L. Halliwell B. et al. 1998). ROS pathologies result from "oxidative stress", i.e. the loss of balance between ROS production and antioxidant defenses: the most serious pathologies that may derive from it are atherosclerosis and various types of tumors. Free radicals are chemical species with an unpaired electron in their outermost orbital and are characterized by their high reactivity and chemical instability. Very important from the biological point of view are the radical species of oxygen and nitrogen such as the superoxide anion $O_2$—., the hydroxyl radical OH, the nitric oxide NO and the peroxynitrite anion ONOO— that can result from the combination of $O_2$—. and NO. radicals. Among the species of oxygen mentioned, the most active is the OH. radical which reacts at few angstroms from the point where it is produced and whose formation can be catalyzed by some transition metals starting from $H_2O_2$. Although there are many free radical formation sites within the cell, it appears that mitochondria are the main source. The superoxide radical is produced above all at the level of the ubiquinone and of the enzyme NADH dehydrogenase. The cell has developed numerous protective mechanisms to limit the production of oxidants and eliminate those in excess. In particular, there are antioxidant enzymes that convert reactive oxygen species into smaller species. The three major antioxidant enzymes are superoxide dismutase (SOD), catalase (CAT), and glutathione peroxidase (GPx). In addition to endogenous antioxidants, free radicals are also inactivated by exogenous or food antioxidants.

It is now widely recognized that the diet used is the basis of a decidedly healthier life, especially when the diet involves the intake of all those substances that are attributed antioxidant properties.

In the context of anti-oxidative and anti-aging processes, particular interest has been addressed, relatively recently, to a peculiar class of substances present in the human organism known as sirtuins.

It is a class of enzyme-activating proteins that act as histone deacetylases or mono-ribosyltransferases. They regulate important metabolic pathways in prokaryotes and eukaryotes. Their name derives from a regulatory silencing yeast gene, implicated in the regulation of cell development.

Sirtuins mediate phenomena such as aging, regulation of transcription, apoptosis, resistance to stress and also affect energy efficiency and vigilance during low caloric intake situations. In short, these substances: show enzymatic properties, regulate the metabolic processes linked to insulin resistance, control immunity, have a fundamental role in epigenetics, and are involved in the defense of cancer diseases.

Their role is similar to that of "sentinel" structures, ready to intervene to activate reparative mechanisms of interventions when DNA damage caused by degradation and therefore aging phenomena is detected dependent, above all, on free radicals.

Numerous studies have also shown that there is an important correlation of direct proportionality between activation of the mechanisms that lead to the production and activation of sirtuins and caloric restriction: more in detail, it has been found experimentally that the caloric restriction can: reduce the incidence and slow down the onset of age-related diseases, by way of non-limiting examples of cardio vascular and neurodegenerative ones; improve stress resistance; and, in general, increase life expectancy.

The reduction of caloric intake favors in fact the expression of genes involved in cellular repair, in protein turnover and synthesis, in resistance to oxidative stress and glucose metabolism.

Among the genes that are activated by caloric restriction are those that encode for sirtuins. As mentioned above, these substances have de-acetylating activity and their activation, at the biological level, involves the maintenance of the organism in a state of health during food shortages. In higher organisms, sirtuins activate lipolysis and gluconeogenesis and control cell proliferation, inflammatory phenomena, those of telomeric aging and stress response. Sirtuins are the expression of SIRT genes, genes normally found in human chromosomes. One of the main substrates of sirtuins are histones, proteins that are part of the composition of chromosomes, where they bind to DNA keeping it compact, organizing it and thus regulating gene expression. Acetylation/de-acetylation of histones modifies the binding of these proteins with DNA allowing the genetic material to interact with other proteins. The sirtuins, in addition to being activated naturally by the caloric restriction, are activated by so-called sirtuin activators. Among these, resveratrol is undoubtedly known, belonging to the family of polyphenolic compounds and present in grape berries, in wine, in some berries and oil seeds (peanut) and in particular plants.

It is of interest to point out that, in order to have medically relevant quantities of such substances, it is not sufficient to consume the indicated foods containing them in the daily diet, because in this case the individual should include several kilos or liters of the specific food in the menu. For these reasons, as will be explained below, the interest is to supply a food with natural extracts containing necessary quantities of STACs-SIRT activators compounds. The Sir2 (Silent information regulator 2) gene, from which the name of the whole family derives, was one of the first longevity genes to be identified in the lower organisms (helminths like the nematode *C. elegans* and midges). Various species, from yeasts to humans, express variants of this gene, whose activation extends life expectancy. Seven genes belonging to this family (SIRT 1-7) have been identified in mammals. In particular, the gene homologous to Sir2 is SIRT1 (Sir2 homolog 1). It encodes the Sirt1 protein, which is able to deacetilate nuclear and cytoplasmic proteins that control critical cellular processes, such as apoptosis and metabolism. SIRT1 regulates the production of insulin and glucose, lipid metabolism and cell survival, hence the deduction that sirtuins can mediate the effects of caloric restriction in mammals (Cohen, Miller et al., 2004). Therefore, the potential anti-aging role of the Sir2 gene, identified for yeasts, also seems to be valid for mammals with more complex mechanisms involving a rich protein pattern. Therefore, caloric restriction promotes cell survival by induction of Sirt1 deacetylase.

Even if it were certain that man could benefit from the anti-aging effects of caloric restriction, the adoption of a chronic dietary diet would not be a viable approach. Researchers have for some time devoted themselves to studies that allow the identification of molecules that can mimic the effects of caloric restriction.

The Sinclair team described 18 plant-derived molecules capable of activating sirtuins in yeasts and studied their effects on SIRT1, the human homologue of Sir2. The flavones quercetin and fisetin, the stilbenes piceatannol and resveratrol and the calcone butein stimulated SIRT1 from 5 to 13 times. The majority of these compounds show a hydroxyl group in meta on the phenolic ring A, trans-oriented to a ring B. When ring A does not show an OH in meta (fisetin), a catechol B ring is necessary to maintain a significant activity. Another important factor for the activity is the coplanarity between the hydroxylated rings A and B.

The most powerful activator was considered to be resveratrol, a compound synthesized by a large number of plants in response to stress, and present in appreciable amounts in grapes and red wine. This molecule is already known for its protective role against many diseases, including cardiovascular, neoplastic and neurodegenerative ones.

Some authors have hypothesized that plants synthesize compounds such as resveratrol in response to stress and restriction of nutrients, so as to activate metabolic pathways involving sirtuins and that fungi and animals in symbiosis with plants stimulate their sirtuins using phenolic derivatives from the plants themselves.

Resveratrol and other STACs (SIR-activating Compounds) activate sirtuins in the nematode *Caenorhabditis elegans* and in *Drosophila melanogaster*, as well as in *S. cerevisiae* yeast.

With regard to aging-related diseases, recent studies have revealed the neuroprotective activity of sirtuins. Resveratrol seems to promote the non-amyloidogenic pathway of the amyloid precursor protein, modulating the pathogenesis of Alzheimer's disease (Thimmappa and Anekonda, 2006).

Recent studies have shown that a resveratrol-like molecule has a higher resveratrol activity compared to substrates. It is pterostilbene, or a stilbenoid chemically bound to resveratrol and also present in blueberries and grapes.

As mentioned above, the adoption of a dietary regimen, and specifically of caloric restriction, in order to promote the activation of sirtuins and, indirectly inhibit the cellular degradation processes due to the action of highly oxidizing chemical species such as free radicals, results in an approach of doubtful feasibility with regard to the constancy of its application which, presumably, would be implemented with relatively limited duration.

In this regard, the purpose of this patent application is to propose a peculiar nutraceutical composition, not to be considered a substitute for meals or food in general, but as a supplement, in order to provide those substances that preliminary studies, which have led to the definition of the present invention, have shown to be particularly active in promoting the activation of sirtuins; in the consistent slowing down of cellular degradation effects; and in the triggering of cellular reparative mechanisms that are macroscopically revealed in a remarkably appreciable body rejuvenation phenomenon.

DESCRIPTION OF THE INVENTION

The present description relates to a peculiar nutraceutical composition suitable for promoting cellular repair in humans following degradation phenomena promoted by the action of oxidizing species and aging-related. The assumption of said composition, under a specific regime, and hereinafter disclosed, results in a visible anti-aging effect in the subject that assumes it. All due to a peculiar combination of substances that, subsisting in said composition, cooperate synergistically giving rise to a resultant holistic in terms of antioxidant and anti-cellular aging properties. More in detail, the nutraceutical composition according to the present invention allows the achievement of the aforementioned effect due to the activation of the sirtuins which, as described above, mediate phenomena such as aging, regulation of transcription, apoptosis, resistance to stress and they also influence energy efficiency and vigilance during low caloric intake situations.

Even more in detail, said composition includes ingredients that, even if taken singly, offer beneficial effects to the body and, when they coexist in particular concentrations, show an enhanced action in the induction of cellular, tissue repair and, macroscopically, in body rejuvenation.

Specifically, the nutraceutical composition according to the present invention comprises ingredients such as honokiol, pterostilbene, polydatin, ellagic acid, zinc, selenium, chromium, vitamin B3.

Honokiol is notoriously a chemical compound extractable from the bark of *magnolia* and that shows many beneficial properties for the organism related to its strong antioxidant action able to counteract the lipid peroxidation and to protect the mitochondria from free radicals. It is also a substance that exerts a protective action against brain functions. Some studies also reveal that it is able to inhibit the mTor path, that is, of the rapamycin receptor that is fundamental for the growth of tumors, without acting in the same direction with the new T lymphocytes that serve to counteract the tumors themselves.

Pterostilbene is a stilbenoid found mainly in blueberries and grapes and belongs to the group of phytoalexins, substances produced by plants to fight infections. It exhibits structure and properties similar to those of resveratrol (belonging to the same family). With respect to the latter, it has two methoxyl groups and shows greater bioavailability; a facilitated transport within the cells; a less rapid degradation and elimination from the organism, in the sense that its half-life within the organism is about seven times higher than that of resveratrol. Pterostilbene also shows beneficial effects on cardiovascular health and cholesterol levels and on cognitive functions, improves concentration and memory and has a calming and anti-stress effect that improves anxiety and nervous tension. Its strong anti-oxidant properties also allow it to inactivate free radicals associated with oxidative stress.

Polydatin is a stilbenoid glucoside derived from resveratrol and mainly present in grape juice. It is more stable and bioavailable than resveratrol because it is more resistant than enzymatic oxidation, it penetrates into cells through an active transport mechanism that uses glucose transporters, is more easily absorbed in the intestine because it is soluble in water. It also shows a strong action against free radicals and, consequently, anti-oxidant, as well as anti-inflammatory. It inhibits lipid peroxidation and is substantially very effective against oxidative stress. This molecule is fifty times more effective than resveratrol because it is totally absorbable as it is water-soluble, unlike resveratrol which is hardly absorbed, thus reducing its bioavailability. Polydatin is a natural molecule that due to an active transport mechanism that uses glucose transporters, reaches all cells, even those of the skin, in very high concentrations.

Ellagic acid is an antioxidant natural phenolic present in numerous fruit and vegetable.

The antiproliferative and antioxidant properties of ellagic acid stimulated research aimed at identifying its potential positive health effects. Zinc is notoriously a constitutive element of many enzymes within the human organism. It is particularly essential for the functioning of enzymes that regulate cellular respiration, and its ability to fight free radicals and reduce the effects of aging is also known.

Selenium is, otherwise, present in small quantities in the body, is largely taken through food and its amount depends on how much it is present in the soil, as in the case of plants. It can be used as an agent for the prevention of many diseases, including cancer, cardio-circulatory dysfunction, arteriosclerosis, cirrhosis, arthritis and emphysema.

Chromium, meaning the trivalent one, is known for its ability to promote the reduction of insulin resistance, the reduction of circulating glucose, with improvement of the optimal blood glucose values, the reduction of blood triglycerides and cholesterol, and the reduction of fat mass, due to the lower availability of circulating glucose, inhibitor of sirtuine activity.

Finally, nicotinamide is an effective detoxifier that, in addition to being an effective agent in the prevention of many diseases, is also effective for the circulation and reduction of cholesterol in the blood. It is fundamental for a correct activity of the nervous system, for the maintenance of skin health and for the formation of the tissues of the digestive system. Nicotinamide (Vit B3) is also a catalyst for the activity of substances such as pterostilbene, polydatin, honokiol.

In the light of the above listed properties of the substances included in the nutraceutical composition according to the present invention, it is evident that the latter is a combination of substances which have undoubted benefits for the organism.

However, its peculiarity does not lie in the individual properties of its components, also known, but in those that derive from their association, including the marked ability to activate the cellular repair mechanisms as a result of damage induced above all by the action of free radicals. Specifically, this effect is due to a synergistic cooperation of the components, and especially those of stilbenoids, in the consistent activation of the sirtuins.

Advantageously, said consistent sirtuin activation results in an equally consistent reparative effect due to oxidative/degradation and cellular aging processes. All with the result of macroscopically observing a visible anti-aging effect.

Advantageously, said effect can be verified after a relatively short period of time from the adoption of a specific regime for the assumption of said composition.

Advantageously, said composition is able to promote the activation of all the sirtuins present in the organism (SIRT 1, 2, 3, 4, 5, 6, 7), due to the presence of its stilbenoid components in the presence of catalysts such as selenium chromium, zinc and vitamin B3 and, simultaneously, to promote the inhibition of the onset of all neurodegenerative diseases.

It is therefore of interest to point out that since the metallic elements are in ionic form in said composition, they contribute to the transport of the SIRT activator extracts through the cell membrane. The ionic form of these elements is therefore strategic precisely because it favors their interaction with the molecules to be conveyed, with the result of promoting transport through the cell membrane.

The result is a composition in which the normal efficiency, which can be found for each individual component, is increased in said composition.

DETAILED DESCRIPTION OF THE INVENTION

The composition according to the present invention comprises the aforementioned ingredients and active ingredients in variable, but specific, concentration ranges, the values of which are translated into the definition of a composition that can be defined as pharmaceutical or, otherwise, a supplement. In any case, the subject composition can be defined as nutraceuticals as it shows therapeutic and preventive properties.

More in detail, said composition comprises from 10% by weight to 15% by weight of honokiol; from 12% by weight to 40% by weight of pterostilbene; from 22% by weight to 32% by weight of polydatin; from 25% by weight to 40% by weight of ellagic acid and from 1.5% by weight to 3% by weight of a mixture of zinc, seleniun, chromium and nicotinamide.

Further, the following excipients may be present.

Preferably, said composition is to be taken in amounts of about 2 g per day corresponding to the contents of two tablets, typically of two oblong tablets.

More in detail, in one of the embodiments thereof, said composition is such that for a tablet the total quantity of the composition ranges between 900 mg and 1200 mg.

In one of the preferred embodiments thereof, said composition, formulated in an oblong tablet, has a weight of 1076 g of which 16 mg are Nicotinamide Vitamin B3; 150 mg are dry extract *magnolia,* 20% titrated in honokiol comprising 30 mg of honokiol; 300 mg of dry extracted blueberry, 20% titrated in pterostilbene comprising 60 mg of pterostilbene; 200 mg of resveratrol from *Polygonum Cuspidatum,* 20% titrated in polydatin comprising 40 mg of polydatin; 400 mg of dry extract pomegranate, 20% titrated in ellagic acid comprising 80 mg of ellagic acid; 10 mg of zinc as zinc gluconate; 0.055 mg of selenium as methionine selenium; 0.040 mg of chromium as chromium picolinate.

Excipients such as microcrystalline cellulose, dibasic calcium phosphate, hydroxypropyl methylcellulose, vegetable stereate magnesium and mixtures thereof may also be included.

The coating agents which can be used to make said tablets are, by way of non-limiting example, hydroxypropylmethyl cellulose, microcrystalline cellulose, stearic acid, titanium dioxide.

The invention claimed is:

1. A nutraceutical composition for the activation of sirtuins in humans consisting of:
   10%-15% by weight of *magnolia* dry extract comprising honokiol;
   12%-40% by weight of blueberry dry extract comprising pterostilbene;
   22%-32% by weight of *Polygonum Cuspidatum* comprising polydatin;
   25%-40% by weight of pomegranate dry extract comprising ellagic acid;
   1.5%-3% by weight of a mixture of zinc, selenium, chromium, and nicotinamide, and
   optionally excipients.

2. The nutraceutical composition according to claim 1, wherein said excipients are included.

3. The nutraceutical composition according to claim 1, wherein said composition has an overall weight comprised between 900 mg and 1200 mg.

4. A nutraceutical composition consisting of 16 mg Nicotinamide (Vitamin B3); 150 mg *magnolia* dry extract comprising 30 mg of honokiol; 300 mg blueberry dry extract comprising 60 mg of pterostilbene; 200 mg *Polygonum Cuspidatum* comprising 40 mg polydatin; 400 mg pomegranate dry extract comprising 80 mg of ellagic acid; 10 mg of zinc ions as zinc gluconate; 0.055 mg of selenium ions as methionine selenium; 0.040 mg of chromium ions as chromium picolinate; and optionally excipients.

5. The nutraceutical composition according to claim 1, wherein said composition comprising excipients selected from the group consisting of microcrystalline cellulose, dibasic phosphate calcium, hydroxypropyl methylcellulose, magnesium stearate and mixtures thereof.

6. The nutraceutical composition according to claim 3, wherein said composition is formulated as an oblong tablet.

7. A method for treating cell aging comprising administering an effective amount of the nutraceutical composition of claim 1, thereby promoting the activation of sirtuins in the cell.

8. The method of claim 7, wherein the method comprises administering a daily dose of 2 g of said composition.

9. A method for treating neurodegenerative diseases; comprising administering an effective amount of the nutraceutical composition of claim 1 to a human subject in need thereof.

10. The nutraceutical composition according to claim 2, wherein said composition has an overall weight comprised between 900 mg and 1200 mg.

11. The nutraceutical composition according to claim 2, wherein said excipients are selected from the group consisting of microcrystalline cellulose, dibasic phosphate calcium, hydroxypropyl methylcellulose, magnesium stearate and mixtures thereof.

12. The nutraceutical composition according to claim 3, wherein said excipients are included and selected from the group consisting of microcrystalline cellulose, dibasic phosphate calcium, hydroxypropyl methylcellulose, magnesium stearate and mixtures thereof.

13. The nutraceutical composition according to claim 4, wherein said excipients are included and selected from the group consisting of microcrystalline cellulose, dibasic phosphate calcium, hydroxypropyl methylcellulose, magnesium stearate and mixtures thereof.

14. The nutraceutical composition according to claim 10, wherein said excipients are selected from the group consisting of microcrystalline cellulose, dibasic phosphate calcium, hydroxypropyl methylcellulose, magnesium stearate and mixtures thereof.

15. The nutraceutical composition according to claim 4, wherein said composition is formulated as an oblong tablet.

16. The nutraceutical composition according to claim 5, wherein said composition is formulated as an oblong tablet.

17. A method for treating cell aging comprising administering an effective amount of the nutraceutical composition of claim 2, thereby promoting the activation of sirtuins in the cell.

18. A method for treating cell aging comprising administering an effective amount of the nutraceutical composition of claim 3, thereby promoting the activation of sirtuins in the cell.

19. A method for treating cell aging comprising administering an effective amount of the nutraceutical composition of claim 4, thereby promoting the activation of sirtuins in the cell.

20. A method for treating cell aging comprising administering an effective amount of the nutraceutical composition of claim 5, thereby promoting the activation of sirtuins in the cell.

* * * * *